United States Patent [19]

Lam et al.

[11] Patent Number: 5,514,146
[45] Date of Patent: May 7, 1996

[54] DEVICE FOR ACCOMODATING AT LEAST ONE SONOGRAPHIC PROBE

[75] Inventors: Arthur M. Lam, Mercer Island, Wash.; Friedemann Kempf, Meersburg, Germany

[73] Assignees: DWL Electronische Systeme GmbH, Sippligen, Germany; University of Washington, Seattle, Wash.; a part interest

[21] Appl. No.: 301,130

[22] Filed: Sep. 6, 1994

[30] Foreign Application Priority Data

Sep. 17, 1993 [DE] Germany ............................ 9314075 U

[51] Int. Cl.⁶ .................................................. A61B 19/00
[52] U.S. Cl. ........................................................... 606/130
[58] Field of Search .................... 128/662.05, 662.06; 606/130

[56] References Cited

U.S. PATENT DOCUMENTS 5,269,305  12/1993  Corol ...................................... 606/130
5,330,485  7/1994  Clayman et al. ....................... 606/130
5,387,220  2/1995  Pisharodi ............................... 606/130

FOREIGN PATENT DOCUMENTS 1438755  11/1988  U.S.S.R. ................................ 606/130

Primary Examiner—Max Hindenburg

[57] ABSTRACT

In a device for accommodating at least one sonographic probe (12) for adjusting it and fixing it on the skull of a patient comprising a support frame (10a) which can be mounted thereto and on which the probe (12) rests adjustably in a probe mounting (44), the support frame (10a) spectacles-like has a nose loop (55) and a pair of holding loops (16a) adjoining same at both sides, wherein two strip-like carrier tongues (38, 38a) are rotatably and longitudinally mounted on each holding loop (16a) and they are connected together at one end by a yoke (42) which is pivoted to them and which is part of the probe mounting (44). The spacing between the nose loop (55) on the one hand and plug-like transverse pins (22) for fixing in the ear region on the other hand is variably adjustable.

18 Claims, 4 Drawing Sheets

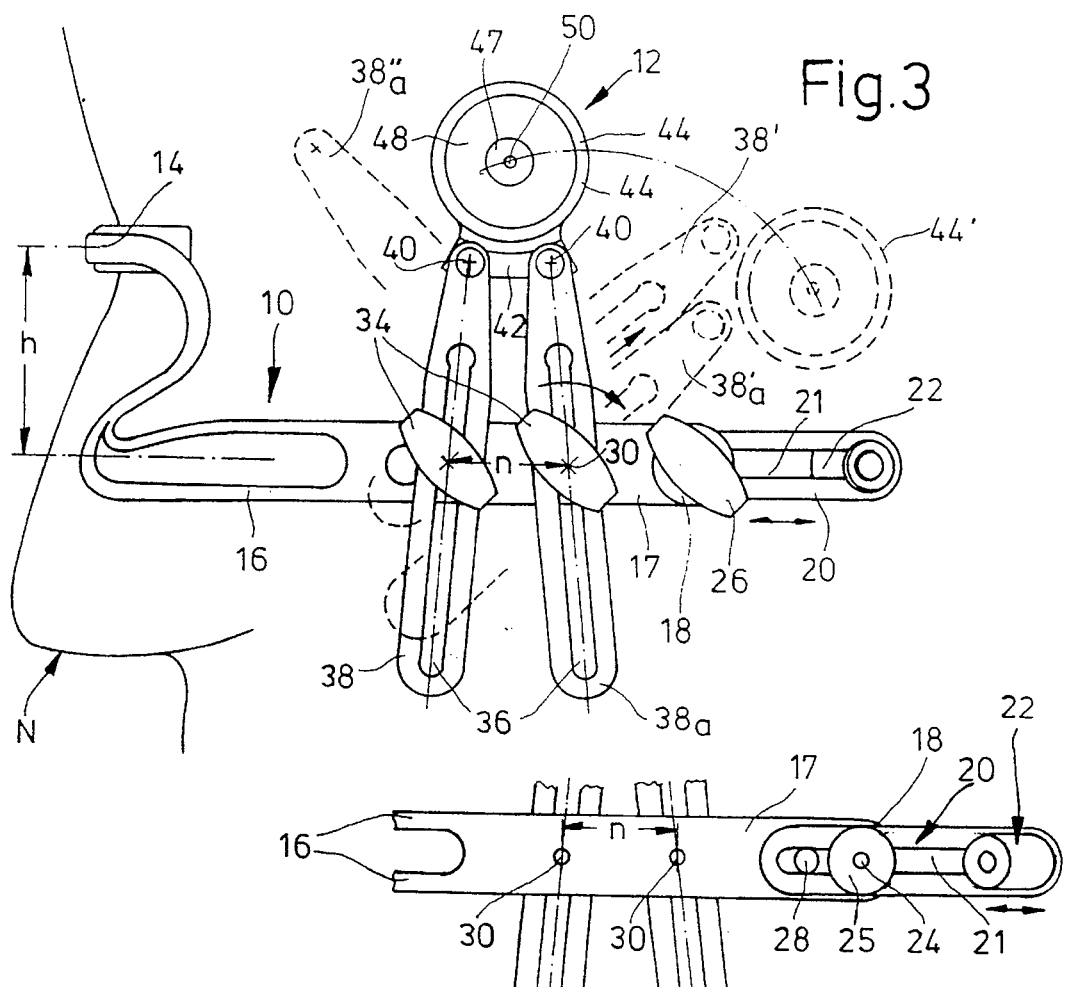
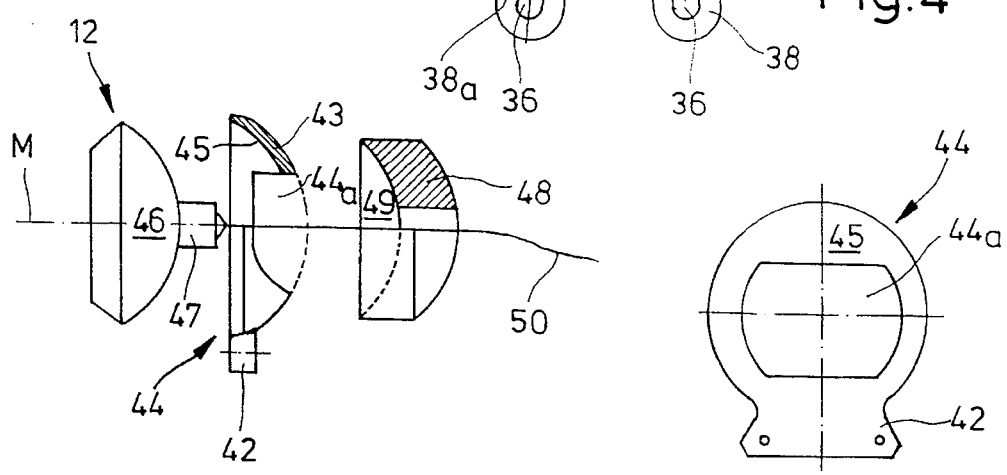

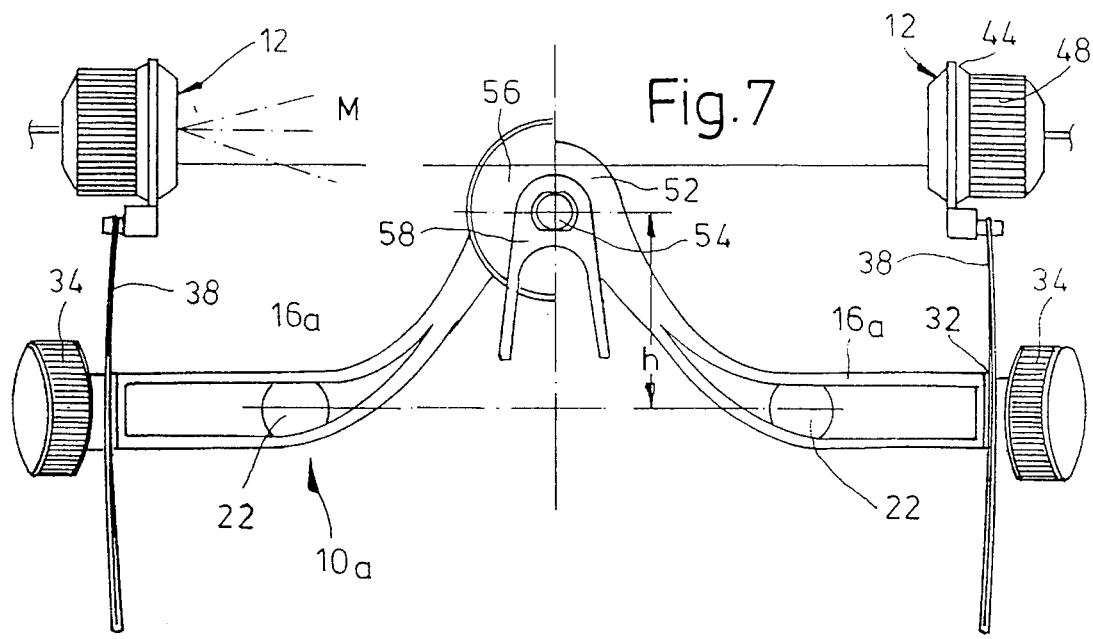
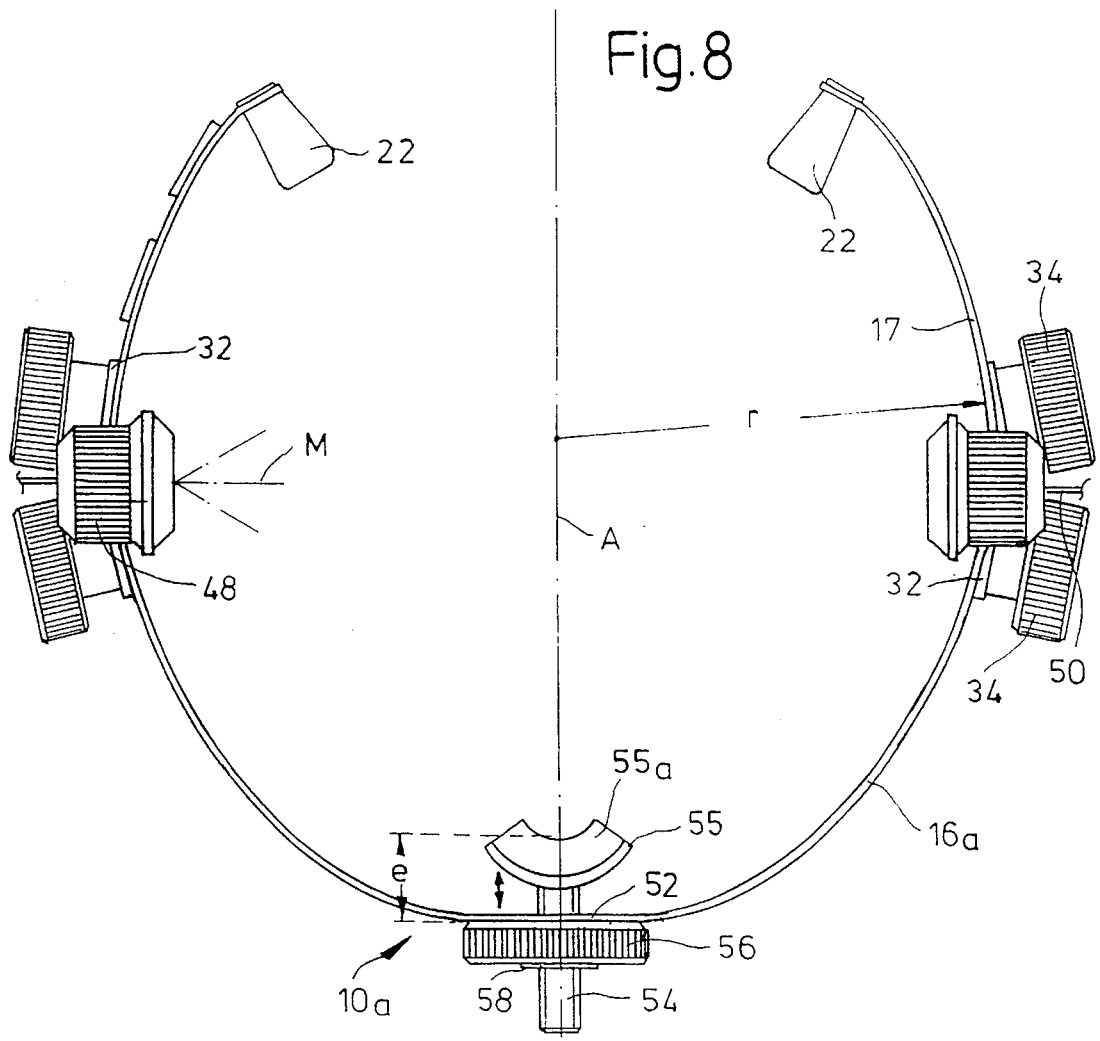

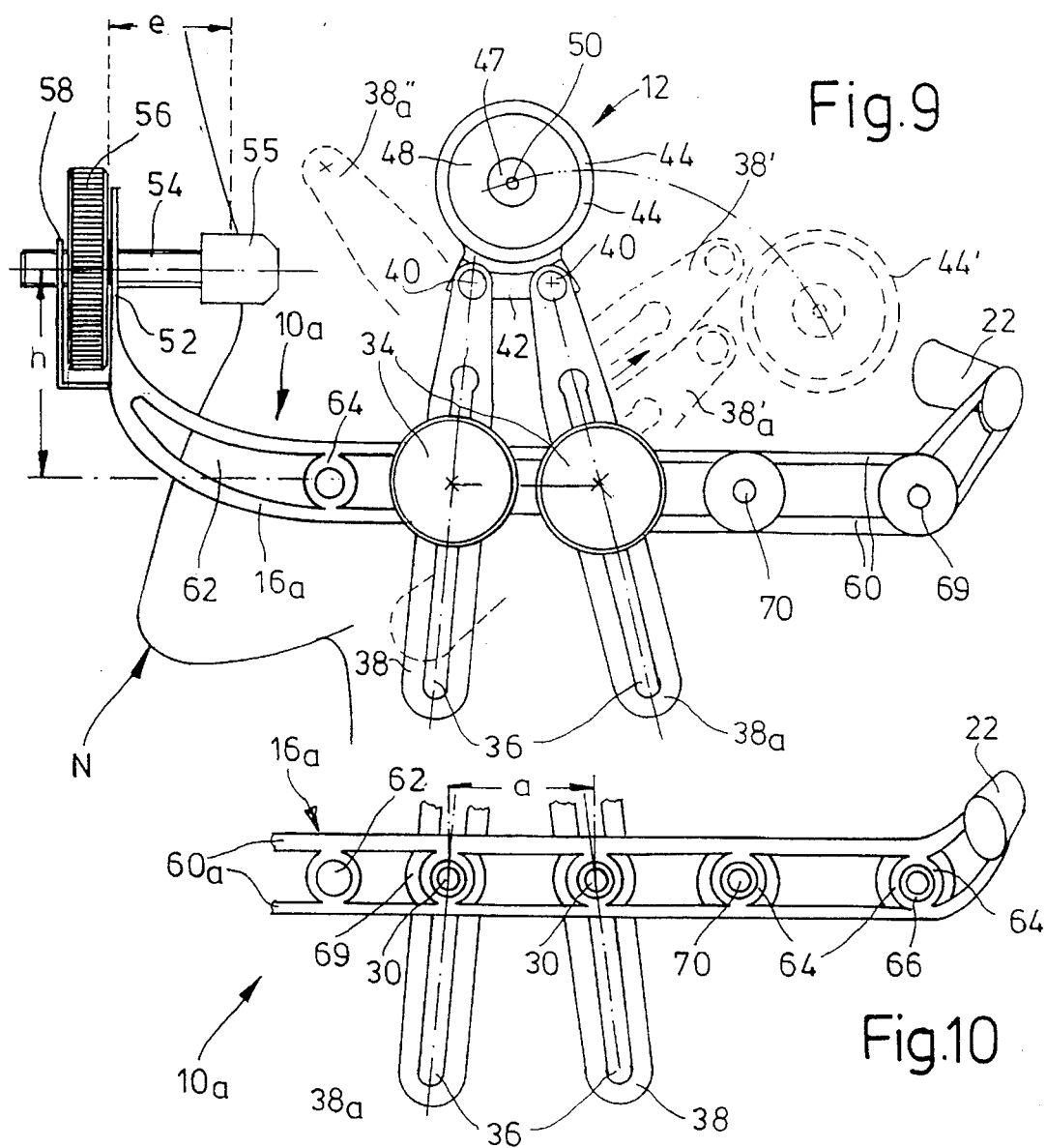
Fig.9
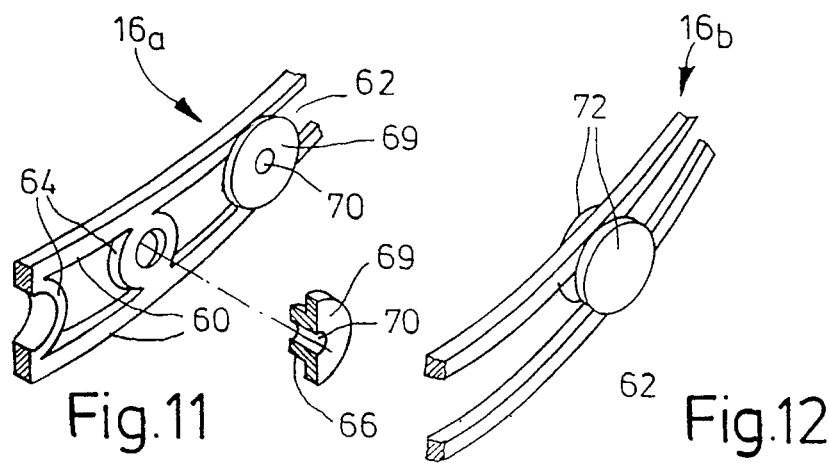
Fig.10
Fig.11 Fig.12

5,514,146

DEVICE FOR ACCOMODATING AT LEAST ONE SONOGRAPHIC PROBE

BACKGROUND AND SUMMARY

The invention concerns a device for accommodating at least one sonographic probe for adjusting it and fixing it to the skull of a patient having a support frame which can be mounted thereto and on which the probe rests displaceably in a probe mounting.

A device of that kind is to be found in the specification of the present applicants' German Utility Model No. 92 10 071, having a holding plate for fixing to the human head, on which holding plate a probe holder is mounted displaceably and fixably at any location with respect to the holding plate. The probe holder includes a holding portion for the probe, mounted pivotably relative to the holding plate in the probe holder.

With knowledge of those facts the inventor set himself the aim of further improving a holding arrangement of the general kind set forth, in particular in regard to adaptation to the measuring window of the skull and simplicity of the device.

That object is attained by the teaching of the independent claim; the appendant claims set forth advantageous developments.

In accordance with the invention the support frame is designed in a spectacles-like configuration with a nose loop and a pair of holding loops which adjoin the nose loop on both sides, wherein the spacing between the nose loop and ear loops or corresponding retaining members that project from the free ends of the support frame is adjustable. Two strip-like carrier tongues are rotatably and longitudinally displaceably mounted on each holding loop, the tongues being connected together at one end by a yoke which is pivoted thereto; the yoke is part of the probe mounting.

The nose loop can be part of the support frame or, in another design configuration, it can be arranged to be variable in respect of spacing relative to the support frame, for adaptation to the shape of the skull of the user.

The two carrier tongues extend approximately parallel to each other in the normal position and can be displaced in any manner in the fashion of the sides of a parallelogram, at one side of which the probe mounting is moved. When the desired skull window has been found, it is only necessary to tighten just onescrew in order to fix the probe mounting on the skull.

In accordance with a further feature of the invention the carrier tongue has a longitudinal slot as a guide for a mounting pin of the side portion about which the carrier tongue is rotatable and on which it is also displaceable over the entire length of the carrier tongue.

So that the spectacles-like support frame can be easily fixed on the skull, projecting from the free ends of the side portions are the retaining members in the form of ear plugs which are inserted into the auditory canal of the patient and which together with the nose loop provide a three-point mounting for the support frame on the skull. There is no longer any need for complicated fixing of the device on the skull.

If the nose loop is part of the support frame, associated with the ends thereof at both sides are telescopic strips which include the ear plugs; the spacing from the latter to the nose loop is variable by virtue of the displaceable telescopic strips, here too for adaptation to the shape of the skull of the user.

DESCRIPTION OF SPECIFIC EMBODIMENT

Further advantages, features and details of the invention are apparent from the following description of preferred embodiments and with reference to the drawing in which:

FIGS. 1 and 7 show front views of two embodiments of a spectacles-like device according to the invention, FIGS. 2 and 8 show plan views of FIGS. 1 and 7 respectively, FIGS. 3 and 9 are a side view of FIGS. 1 and 2 and FIGS. 7 and 8 respectively, FIGS. 4 and 10 are an inside view of a part of the configuration of the device in a view corresponding to FIGS. 3 and 9 respectively, FIG. 5 is a partly sectional side view on an enlarged scale of a detail from FIGS. 1 and 7, FIG. 6 is a front view of a part of FIG. 5, and FIGS. 11 and 12 are perspective views of two different configurations of a portion of the device.

DESCRIPTION OF THE DRAWING

Two probes 12 which are directed towards each other for medical ultrasound diagnosis of the human skull are disposed on a spectacles-like support frame 10 at an axial spacing a from each other, which is indicated in the drawing on approximately natural scale.

The support frame 10 has a nose loop 14, which is crossed by an axis of symmetry A, for a human nose which is diagrammatically shown at N, while a holding loop 16 is formed on the nose loop at each of the two sides thereof.

Figure 1:
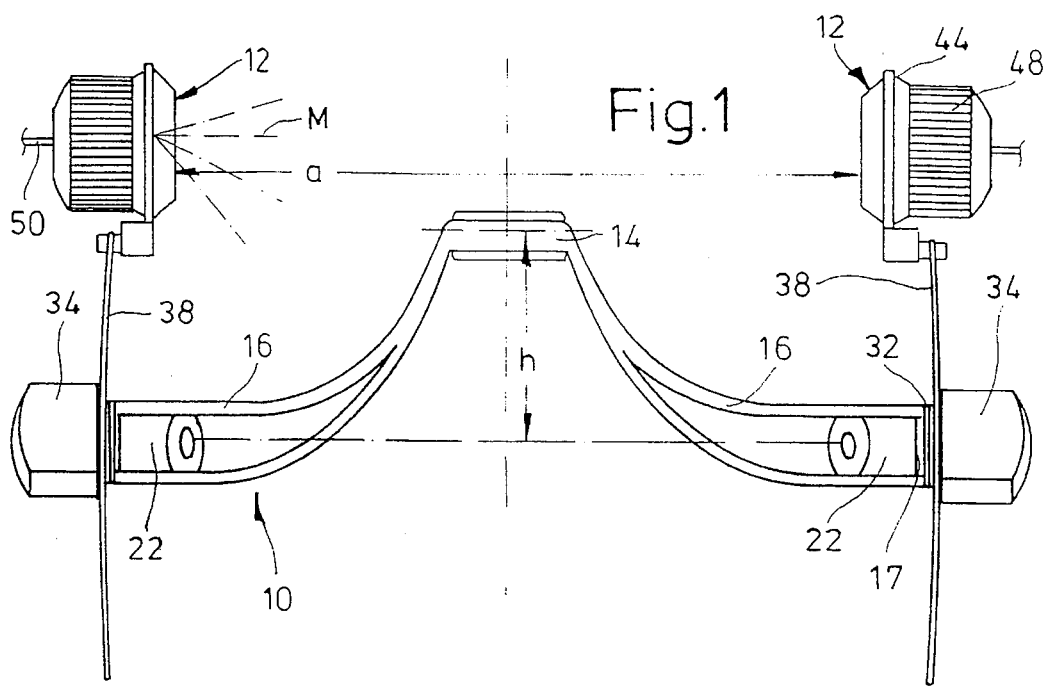
In FIG. 1 the holding loop 16 extends from the nose loop 14 in a part-circular curve of a height h of for example 30 mm downwardly to portions of the holding loops 16, which are horizontal in FIGS. 1 and 3; they terminate in the form of side portions 17 which can be resiliently applied to the temples of the human head.

Extending through a longitudinal slot 21 in the telescopic strip 20 is a screw pin 24 which is screwed both into a slide plate 25 which is displaceable in the longitudinal slot 21 and also into a rotary knob 26, at the outer side of the support frame 10, and serves for clampingly fixing the telescopic strip 20 to the side portion 17 of the holding loop 16 between the slide plate 25 and the above-mentioned plate-like shaped end portion 18. A guide pin 28 which projects from the holding loop 16 also slides in the longitudinal slot 21, for parallel guidance in the thrust movement.

Disposed in each of the side portions 16 at a spacing n from each other are two mounting pins 30 which each pass through a plate-like shaped portion 32 formed on the respective holding loop 16 and which are each fitted with outwardly projecting screw ends into a rotary knob 34.

Each mounting pin 30 passes through the central longitudinal slot 36 of a carrier tongue 38, 38a; both are rotatable about their mounting pins 30 and are longitudinally displaceable thereon. In addition at their end which is the upper end in the drawing, they are each pivoted to a yoke 42 by a screw 40.

Figure 2:
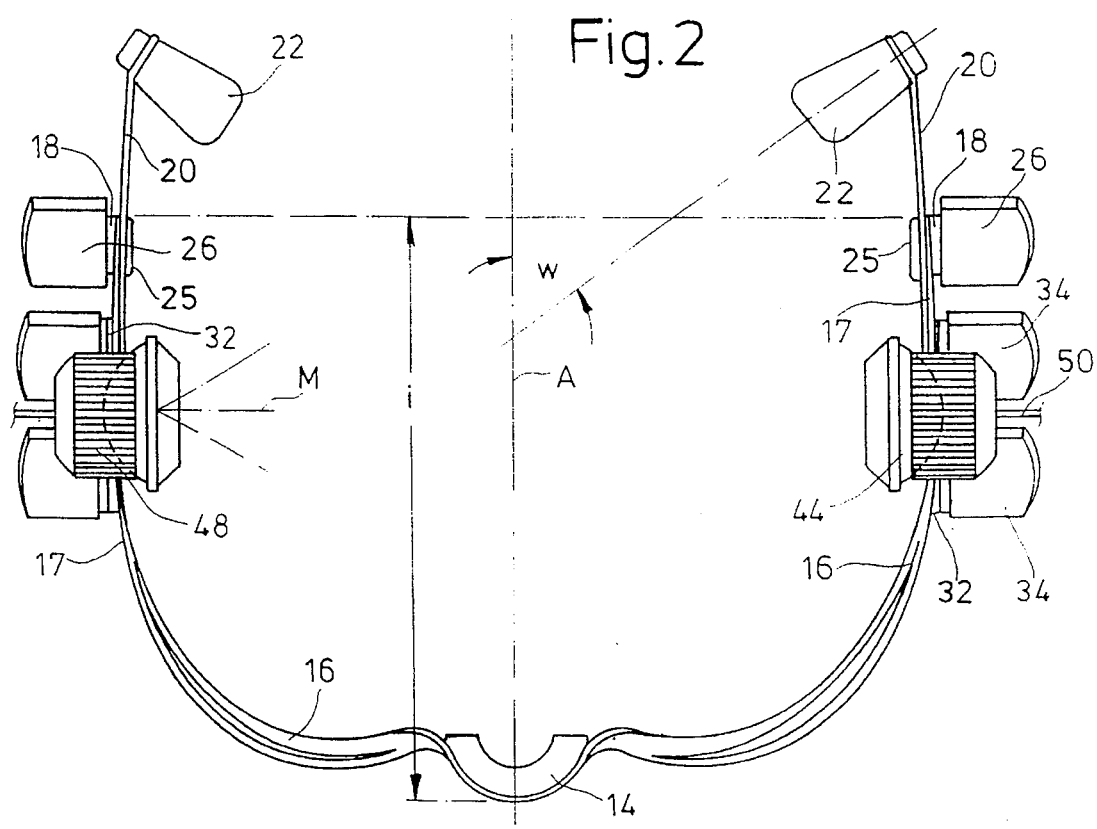
In FIG. 2 the side portions go into a plate-like rounded end 18, at a horizontal spacing i from the nose loop 14. A telescopic strip 20 is fitted to each of the side portions 17 in such a way as to be displaceable in parallel relationship, the telescopic strip carrying an ear plug 22 which serves for fixing the support frame 10 to the human ear. In the fixing position of the support frame at three points—at the human nose N and the ears which are not shown in the drawing—the side portions 17 of the support frame 10 extend substantially horizontally. For the purposes of better fixing, the ear plug 22 faces at an angle w to the axis of symmetry A towards the nose loop 14 (see FIG. 2).

The yoke 42 is part of a mounting shell 44 which is preferably formed from plastic material, as a probe mounting; it resembles a ring with a central opening 44a and a spherical inside surface 45 to which a part-spherical surface 46 of the probe 12 closely fits and at which the latter is thus adjustably fixed; possible directions of the center line M of the probe are indicated in FIGS. 1 and 2. The two carrier tongues 38, 38a, with the yoke 42, form a parallelogram-like adjustment arrangement for the probe mounting 44.

A tubular screw connecting portion 47 which is coincident with the probe center line M (FIG. 5) is seated in a screw ring 48 which in turn approximately bears with a spherical inside surface 49 against the corresponding outside surface 43 of the mounting shell 44 and—in the central opening 44a thereof—the part-spherical surface 46. A probe line 50 is extended outwardly through the tubular screw connecting portion 47 and is connected to an evaluation unit in a manner not shown in the drawing.

FIG. 3 shows the pivotal movement of the adjusting arrangement about the mounting pin 30 which is at the right therein; the carrier tongue 38a is rotated and moves into the position 38a', and the other carrier tongue 38 is rotated in approximately parallel relationship and at the same time displaced on its mounting pin 30 in the direction indicated by the arrow to position 38' until the mounting shell 44 is at 44'. Another position of the carrier tongue 38a can be seen at 38a".

By virtue of the described manner of mounting the probe 12 it can be adjusted on the head and can be adapted to the respective topographic conditions of the patient; for ultrasound diagnosis in the interior of the skull, it is necessary to find thereon the position for the probe 12 which permits transcranial investigation.

In that procedure the evaluation or Doppler unit which is switched on is connected to the probe 12 and the system for Doppler sonography is therefore already in operation so that the doctor can precisely trace at what location on the skull, that is desirable for the intended ultrasound investigation, the probe 12 is precisely to be found; the probe is then fixed there in the described manner by rotating the rotary knobs 34. The surface of the probe automatically orients itself by virtue of the spherical sliding surfaces 45/46 and 43/49.

In the embodiment shown in FIGS. 7 through 10 the support frame 10a has a part-circular holding loop 16a of radius r. The holding loop 16a is in one piece, that is to say the telescopic strip 20 of the other configuration is here fixedly integrated into the holding loop 16a and the ear plugs 22 are fixedly connected to the holding loop 16a. Here, instead of the nose loop, the arrangement has a plate 52 which is also integrated into the holding loop 16a (right-hand half in FIG. 7), while a non-rotatably fixed adjusting screw 54 passes through the plate 52 and can be displaced in a control wheel 56. The control wheel 56 is provided between the plate 52 and a holding limb 58 which is formed thereon. The adjusting screw 54 terminates at the inside of the support frame in the form of a channel 55 with foam insert 55a; the latter is fitted on to the nose A of the user—the support frame 10a is then easily adjustable in respect of spacing relative to the nose N by virtue of the adjusting screw 54 (spacing e between the adjusting wheel 56 and the channel 55).

The holding loop 16a comprises two edge bars 60 which at one end converge towards the plate 52 and at the other end towards the ear plugs 22 and which form between them a longitudinal slot 62. The slot is interrupted in FIGS. 7 through 11 by rings 64 which are formed therein and into which are inserted screw bushes 66 of disks 69 arranged at the outsides of the loop. The respective central screw hole 70 of each disk 69 accommodates a mounting pin 30.

In the construction shown in FIG. 12 the edge bars 60 are not connected by the rings 64; here the longitudinal slot 62 forms a guide track for an adjusting screw (not shown) which connects a pair of clamping plates 72. They can be fixed in the holding loop 16b steplessly with adjoining carrier tongue 38, 38a.

We claim:

1. A device for accommodating at least one sonographic probe for adjusting said probe and for fixing the same to a patient's skull, said device having a support frame which can be mounted to a skull, and on which frame the probe rests displaceably in a probe mounting, said support frame comprising:

a nose loop and two holding loops adjoining said nose loop at both sides thereof in a spectacles-like manner, a pair of strip-like carrier tongues provided for each of said holding loops, for passing rotatably and longitudinally displaceably through the same, wherein said pair of carrier tongues is pivotably connected at one end by a yoke, and wherein said yoke is part of said probe mounting.

2. The device as set for the in claim 1, wherein said support frame further comprises a plug-like transverse pin projecting from each of the free ends of the support frame, the distance between said transverse pin and said nose loop being adjustable.

3. The device as set forth in claim 2, wherein said plug-like transverse pin faces towards a respective other holding loop connected to said support frame.

4. The device as set forth in claim 1, wherein each of said holding loops comprises a pair of mounting pins, and each of said carrier tongues has a longitudinal slot as a guide means for one of said mounting pins, for clamping said carrier tongues to said holding loops.

5. The device as set forth in claim 4, wherein a spacing of said pair of mounting pins approximately corresponds to a spacing of connecting points of carrier tongues to said yoke.

6. The device as set forth in claim 4, wherein said carrier tongues are disposed displaceably with said yoke on said holding loop of the support frame in a parallelogram-like manner.

7. The device as set forth in claim 1, wherein the distance between said nose loop and said holding loops is adjustable.

8. The device as set forth in claim 7, wherein said nose loop is part of a screw element passing through said support frame.

9. The device as set forth in claim 8, wherein said support frame further comprises a screw wheel rotatably mounted on said support frame, said screw element passing through said screw wheel.

10. The device as set forth in claim 1, wherein said holding loop comprises a side portion, and further comprises a telescopic stripe for extending the same, said telescoping strip being provided displaceably and parallel to said side portion, wherein said plug-like transverse pin is provided on a free end of said telescopic strip.

11. The device as set forth in claim 10, wherein said plug-like transverse pin defines an angle with an axis of symmetry of said support frame, said angle being open to a side opposite to said nose loop.

12. The device as set forth in claim 1, wherein said holding loops are disposed displaceably relative to said nose loop in respect of height on said support frame.

13. The device as set forth in claim 1, wherein each of said holding loops comprises a pair of edge bars, said edge bars defining a longitudinal slot therebetween.

14. The device as set forth in claim 13, wherein said edge bars are connected by a plurality of rings, said rings being disposed in a plane of said edge bars.

15. The device as set forth in claim 13, wherein said edge bars provide a guide track for clamping devices.

16. The device as set forth in claim 1, wherein said probe mounting comprises a spherical surface for bearing against a sliding surface of probe, said probe being movable at said spherical surface, and having a correspondingly shaped sliding surface, and wherein said yoke comprises a central opening.

17. The device as set forth in claim 16, wherein said probe mounting is ring-shaped with inner and outer spherical surfaces, said probe being mountable to one of said surfaces, and wherein said probe mounting further comprises a screw ring to be connected to said probe, said screw ring being provided mountable to said other spherical surface.

18. The device as set forth in claim 17, wherein said probe and said screw ring are connected by a tubular element, said tubular element being displaceable in said central opening.

* * * * *

UNITED STATES PATENT AND TRADEMARK OFFICE
CERTIFICATE OF CORRECTION

PATENT NO. : 5,514,146
DATED : May 7, 1996
INVENTOR(S) : Arthur M. Lam et al

It is certified that error appears in the above-indentified patent and that said Letters Patent is hereby corrected as shown below:

Col. 4, line 33 change "for the" to --forth--.

Col. 6, line 3 insert --a-- after "of".

Signed and Sealed this

Thirteenth Day of August, 1996

Attest:

BRUCE LEHMAN

Attesting Officer     Commissioner of Patents and Trademarks